(12) United States Patent
Labban et al.

(10) Patent No.: US 9,610,142 B1
(45) Date of Patent: Apr. 4, 2017

(54) ADJUSTABLE BITE RECORDING TOOL FOR DENTAL IMPLANTS

(71) Applicant: KING SAUD UNIVERSITY, Riyadh (SA)

(72) Inventors: Nawaf Yousef Ibrahim Labban, Riyadh (SA); Hanan Nejer Sahil Alotaibi, Riyadh (SA)

(73) Assignee: King Saud University, Riyadh (SA)

( * ) Notice: Subject to any disclaimer, the term of this patent is extended or adjusted under 35 U.S.C. 154(b) by 76 days.

(21) Appl. No.: 15/001,212

(22) Filed: Jan. 19, 2016

(51) Int. Cl.
*A61C 9/00* (2006.01)
*A61C 8/00* (2006.01)
*A61C 19/05* (2006.01)

(52) U.S. Cl.
CPC ............ *A61C 8/0001* (2013.01); *A61C 19/05* (2013.01)

(58) Field of Classification Search
CPC ..... A61C 8/0001; A61C 19/05; A61C 8/0068; A61C 8/0075; A61C 8/0078; A61C 8/0089; A61C 8/005; A61C 9/00; A61C 9/002; A61C 13/34
See application file for complete search history.

(56) References Cited

U.S. PATENT DOCUMENTS

| | | | |
|---|---|---|---|
| 5,597,303 A | 1/1997 | Simmons | |
| 5,947,736 A | 9/1999 | Behrend | |
| 2012/0052463 A1 | 3/2012 | Pollet | |
| 2012/0100503 A1* | 4/2012 | Blackbeard | A61C 8/005 433/174 |
| 2012/0202169 A1 | 8/2012 | Ryu et al. | |
| 2013/0157217 A1 | 6/2013 | LeBeau | |
| 2013/0203009 A1 | 8/2013 | Mutsafi et al. | |
| 2015/0289952 A1 | 10/2015 | Hochman et al. | |

FOREIGN PATENT DOCUMENTS

KR 1020070099257 A 10/2007

* cited by examiner

*Primary Examiner* — Heidi M Eide
(74) *Attorney, Agent, or Firm* — Richard C. Litman

(57) ABSTRACT

The adjustable bite recording tool for dental implants includes a support post having opposing upper and lower ends. The threaded portion of a screw extends downward from the support post and is adapted for releasable attachment to the patient's pre-existing dental implant. An angularly adjustable ring is mounted on the support post. A support arm extends upward from the angularly adjustable ring at an oblique angle, and a support table is mounted on an upper end of the support arm. A bite recording cap is mounted on the support table and on the upper end of the support post. A top surface of the bite recording cap is adapted for receiving a bite recording medium.

20 Claims, 5 Drawing Sheets

ADJUSTABLE BITE RECORDING TOOL FOR DENTAL IMPLANTS

BACKGROUND OF THE INVENTION

1. Field of the Invention

The present invention relates to dental measurements, and particularly to an adjustable bite recording tool for recording a relationship between dental implants and opposing maxillary or mandibular teeth or other dental implants.

2. Description of the Related Art

Tooth replacement, specifically by dental implantation, is a procedure for treating or preventing oral conditions, such as volumetric changes of soft and hard tissues, shifting of surrounding teeth, damage to roots of adjacent teeth and deterioration of the jawbone, as well as aesthetic issues. Typically, a dental implant has an externally threaded post that is surgically implanted in either the patient's maxilla or mandible. The bone adheres to the external threads during post-surgical healing so that the dental implant becomes osteointegrated into the bone. The dental implant defines an internally threaded bore. A customized replacement crown can be attached directly to the dental implant by fastening a screw into the bore, or an abutment can be attached to the dental implant and the replacement crown can be mounted on the abutment. In order to ensure that the replacement crown in made so that the replacement crown is in proper occlusal relation with the corresponding existing opposing tooth in either the maxilla or the mandible, the dentist will rely on bite registration or dental impressions to make the appropriate measurements or molds so that the patient will have a normal or natural bite after installation of the replacement crown. In both cases, an elastic (typically crosslinking) material is used to copy part or all of a person's dentition (i.e., hard as well as soft tissue) and other areas of the mouth. A great deal of time and effort is expended by dentists and dental technicians in preparing accurate crown implants, specifically due to the complexities involved.

Registration and impression procedures, especially in multiple tooth replacements, often end up with some inaccuracies, and additional time and effort must be invested. The process often involves several trial-and-error procedures. Such inaccuracies may cause misalignment of bite and jaws, resulting in improper functionality, aesthetics and possibly even temporomandibular joint disorder (TMJ), a painful condition that can affect the head, neck, jaw and shoulders.

Typical tools used for recording occlusal bite have a unitary construction; i.e., they are not adjustable. This is why inaccuracies and subsequent procedures are so common. It would obviously be desirable to provide an adjustable tool for assisting in bite registration, particularly in difficult situations, for example, in the case of an arch with a Kennedy classification I/II opposing an arch with a similar Kennedy classification or natural teeth. Thus, an adjustable bite recording tool for dental implants solving the aforementioned problems is desired.

SUMMARY OF THE INVENTION

The adjustable bite recording tool for dental implants includes a support post having opposing upper and lower ends, and an annular groove formed in an external wall of the support post adjacent the lower end thereof. The threaded portion of a screw extends downward from the support post and is adapted for releasable attachment to the patient's pre-existing dental implant.

An angularly adjustable ring is mounted on the support post within the annular groove so that the ring may be selectively rotated with respect to the support post. A support arm extends angularly upward from the ring, and a horizontal support table or platform is mounted on an upper end of the support arm. A bite recording cap is mounted on the horizontal support table and the upper end of the support post. The top surface of the bite recording cap is adapted for receiving a bite recording medium, e.g., silicone, for forming the bite impression of the tooth positioned opposite the patient's dental implant.

These and other features of the present invention will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
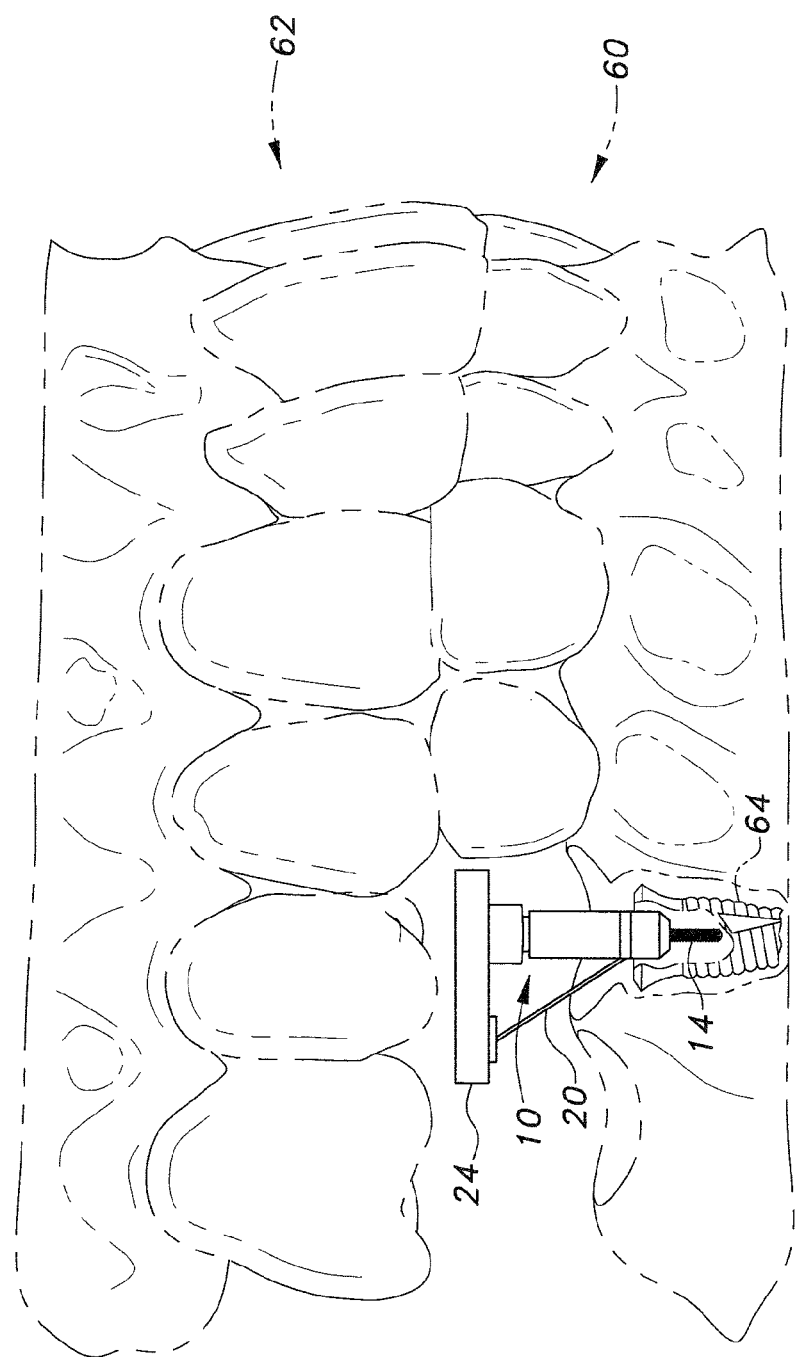
FIG. 1 is an environmental side view of an adjustable bite recording tool for dental implants according to the present invention, shown with the dental implant broken away to show details of the tool.

As shown in FIG. 1, the adjustable bite recording tool for dental implants 10 is used to form a bite impression of a tooth positioned opposite a patient's dental implant. In FIG. 1, the adjustable bite recording tool 10 is shown engaging a dental implant 64 positioned in the patient's mandibular arch 60 for forming a bite impression from an opposing molar in the patient's maxillary arch 62. It should be understood that this particular positioning is shown for illustrative and exemplary purposes only.

Figure 2:
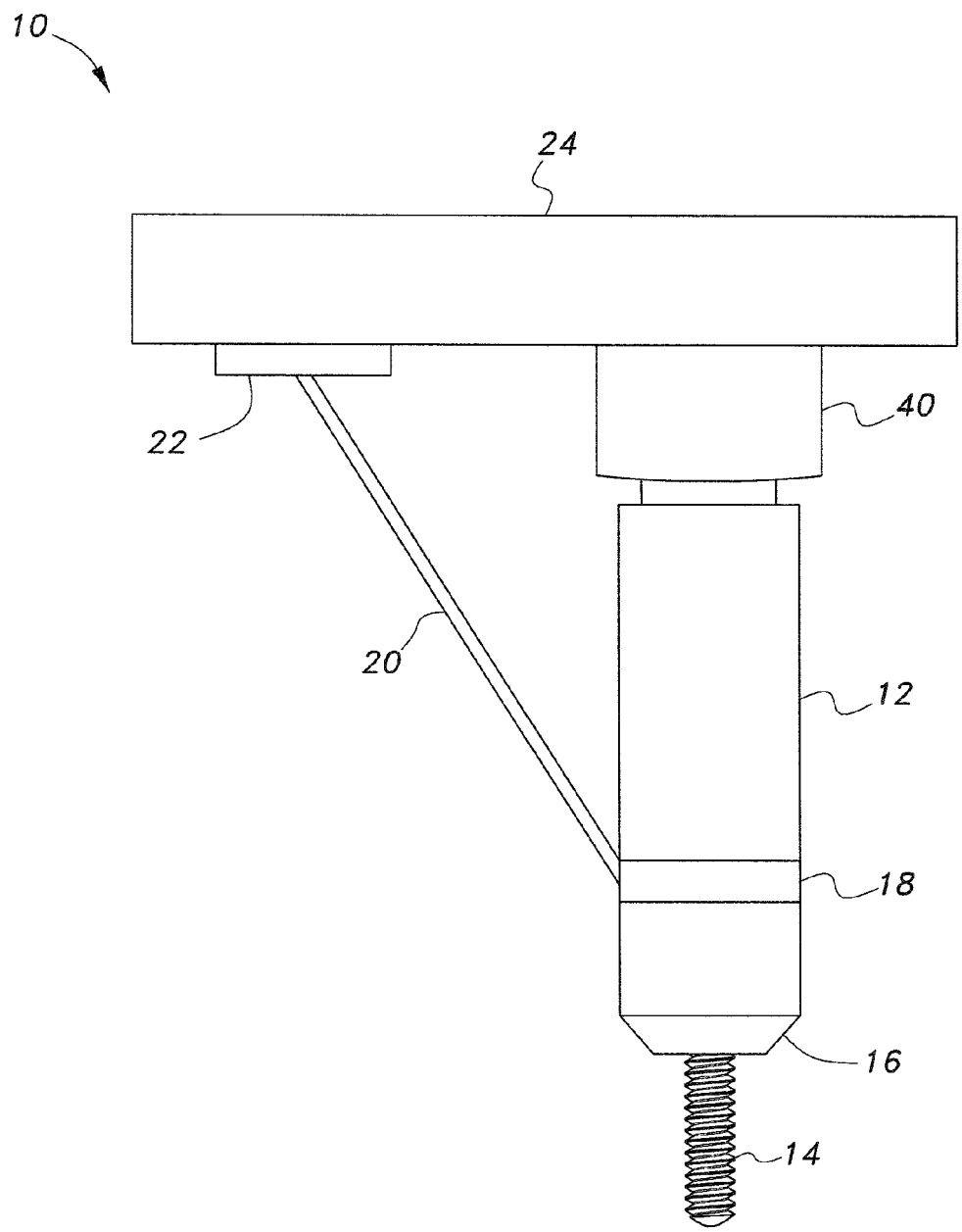
FIG. 2 is a side view of the adjustable bite recording tool of FIG. 1.
Figure 4:
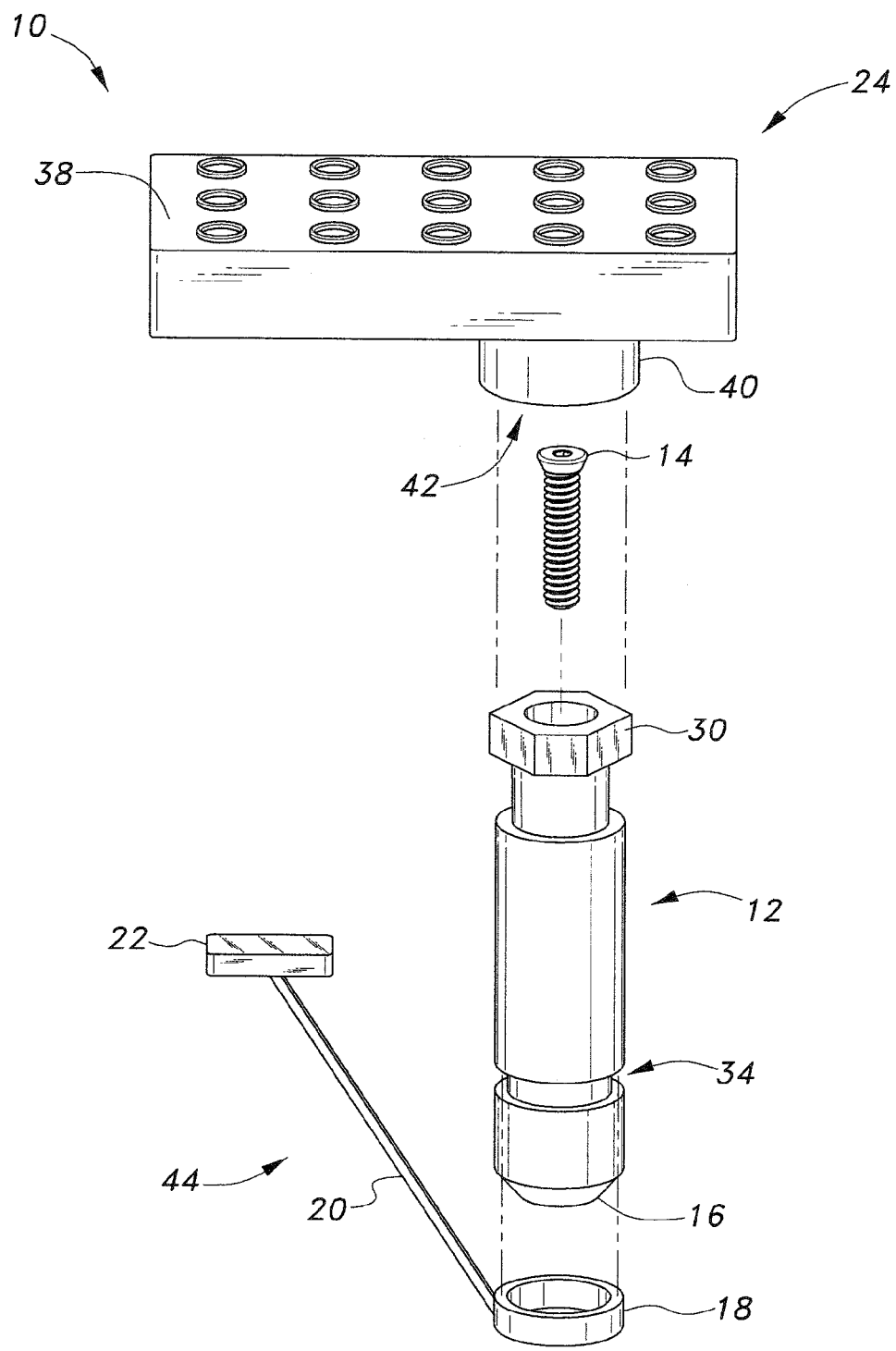
FIG. 4 is an exploded perspective view of the adjustable bite recording tool of FIG. 1.

As best seen in FIGS. 2 and 4, the adjustable bite recording tool for dental implants 10 includes a bite post or support post 12 having opposing upper (superior) and lower (inferior) ends, 30, 16, respectively, and an annular groove 34 formed in an external wall 70 of the support post 12 adjacent the inferior or lower end 16. The post 12 is hollow, and a screw 14 is inserted into the support post 12 so that the threaded shank or shaft extends from the lower end 16 through a hole 28 in the inferior or lower end 16 of the support post 12. As shown in FIG. 1, the threaded portion of screw 14 is adapted for fastening to the threaded internal bore of the patient's pre-existing dental implant 64. The support post 12 has a hexagonal superior or upper end 30. The main body of the post 12 is preferably cylindrical. The lower or inferior end 16 of the post 12 is preferably tapered or frustoconical, but may have any configuration or shape required to closely engage the upper surface of the dental implant 64. The support post 12 can be formed from any metal that can be autoclaved for sterilization and reuse.

Figure 3:
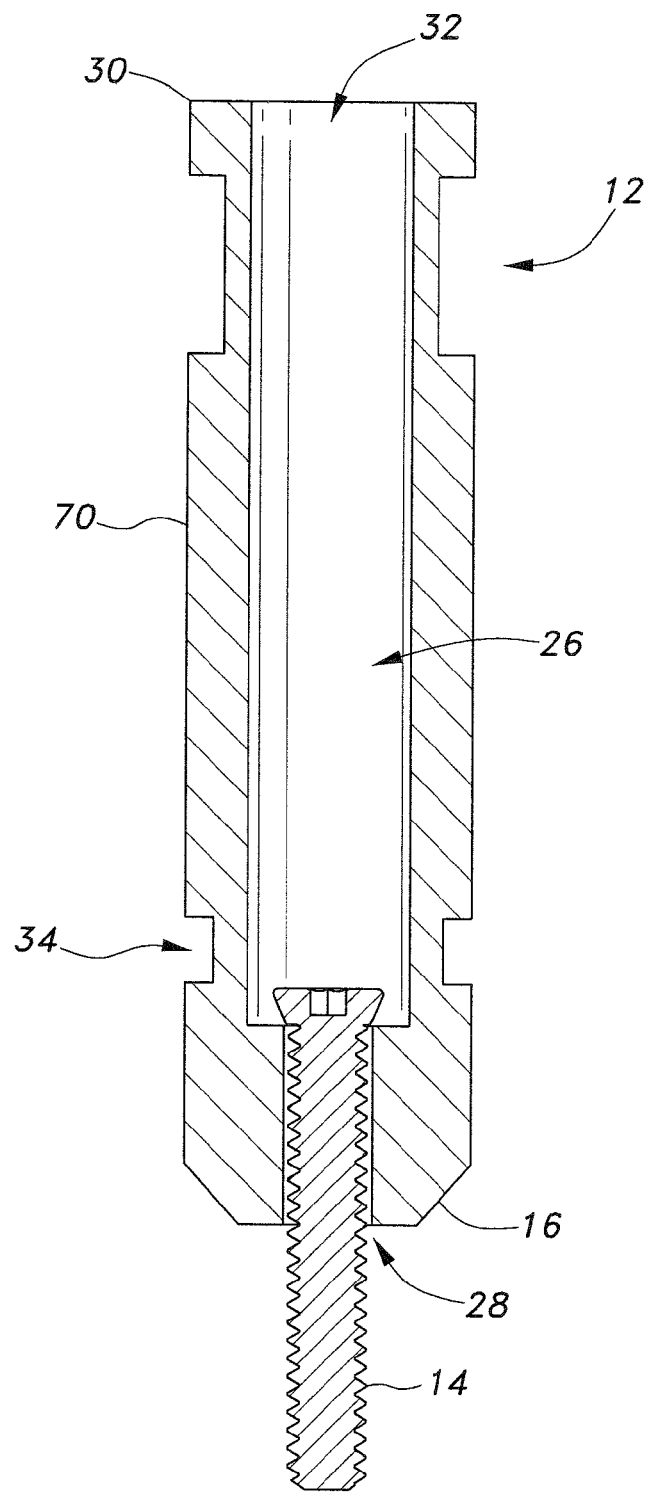
FIG. 3 is a side view in section of a support post of the adjustable bite recording tool of FIG. 1.

As shown in FIG. 3, the support post 12 is preferably hollow. The upper end 30 defines an opening 32, and the lower end 16 similarly defines an opening 28, thus forming a passage 26 for the shaft of the screw 14. As shown, the threaded portion of the screw 14 projects through the lower end 16 of the support post 12. The head of the screw 14 is retained within the hollow support post 12. It should be understood that support post 12 and screw 14 may be manufactured in a variety of sizes, configurations, and relative dimensions in order to mate with any suitable type of dental implant 64.

An angularly adjustable ring 18 is mounted on the support post 12 within the annular groove 34, so that the angularly adjustable ring 18 may be selectively rotated with respect to the support post 12. The lower end of a support arm 20 extends from the angularly adjustable ring 18, and a horizontal support ledge or table 22 is mounted on an upper end of the support arm 20. The support arm 20 is preferably square in cross section. As shown in FIG. 4, the angularly adjustable ring 18, the support arm 20 and the horizontal support 22 are preferably integrally formed with one another, forming an integral support member 44.

A bite recording cap 24 is selectively mounted on the horizontal support 22 and the upper end 30 of the support post 12. The bite recording cap 24 preferably includes both an upper platform portion 38 and a lower sleeve portion 40. The lower sleeve portion 40 of the bite recording cap 24 preferably has a hexagonal socket or recess 42 formed therein for receiving the hexagonal upper end 30 of the support post 12. The upper end 30 of support post 12 is preferably configured for mating with a matching polygonal configuration of the recess 42. In FIG. 4, the upper end 30 is shown as having a substantially hexagonal configuration, although it should be understood that this is shown for exemplary purposes only.

Figure 5:
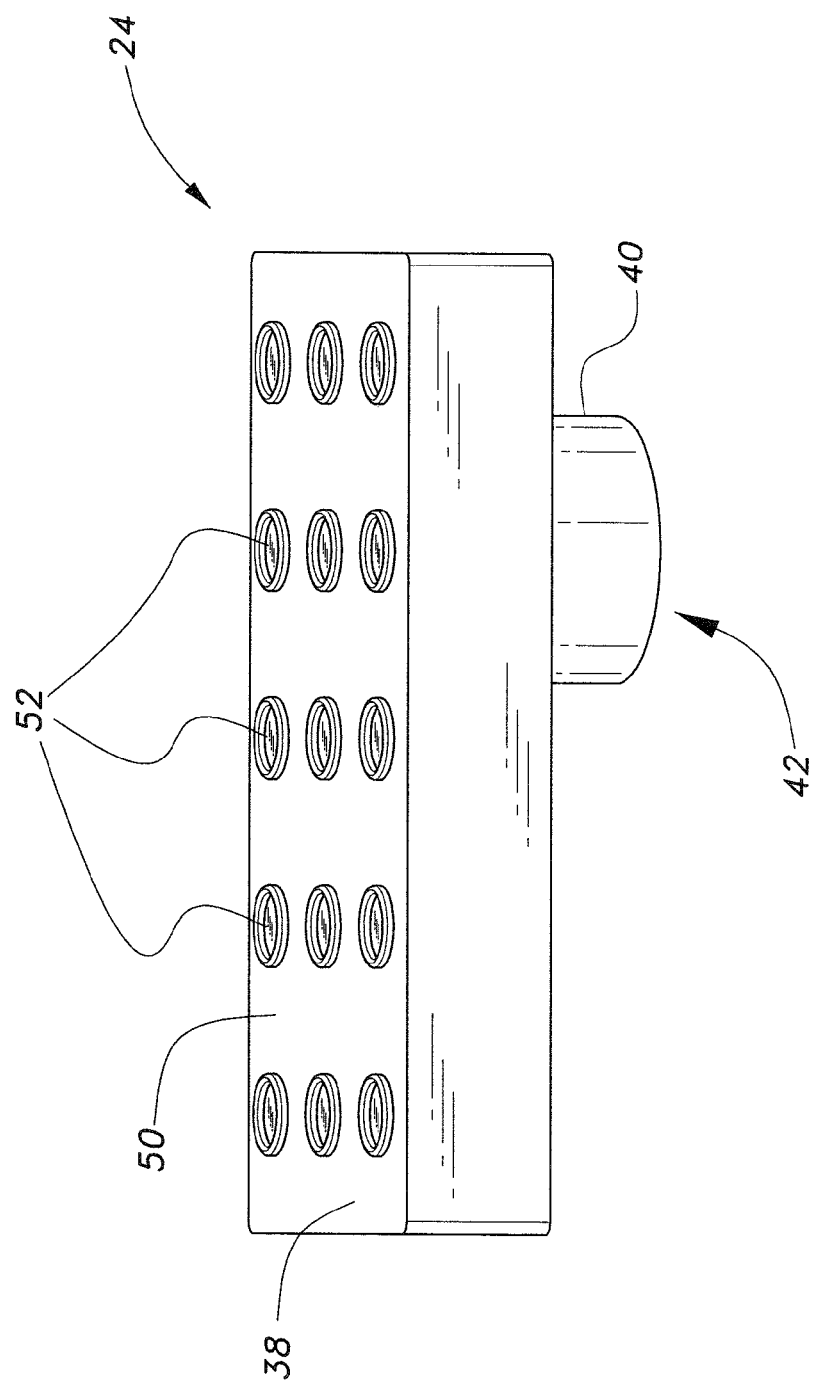
FIG. 5 is a perspective view of a bite recording cap of the adjustable bite recording tool of FIG. 1.

The top surface 50 of the upper platform portion 38 of the bite recording cap 24 is adapted for receiving a bite recording medium (e.g., silicone) or forming the bite impression of the tooth positioned opposite the patient's dental implant 64. Preferably, the top surface 50 of the bite recording cap 24 is textured for releasably engaging the bite recording medium. As shown in FIG. 5, an array of recesses 52 may be formed in the top surface 50 for frictionally engaging the bite recording medium. It should be understood that the bite recording cap 24 may be used in combination with any conventional bite recording medium, such as silicone bite registration material or the like. Although the bite recording cap 24 may be made from any suitable material, a plastic or similar material is preferably used, allowing the bite recording cap 24 to be easily modified or resized using acrylic bur or the like.

In use, as illustrated in FIG. 1, once the adjustable bite recording tool for dental implants 10 has been secured to dental implant 64, the support arm 20 may be rotated to place the support table 22 in the desired position. The bite recording cap 24 is placed on the support table 22 and the sleeve 40 is placed over the top of the post 12, the hexagonal recess 42 in the sleeve 40 mates with the hexagonal superior end 30 of the post 12 to prevent the cap 24 from rotating while the impression is being made. The silicone bite registration material is injected onto the top surface 50 of the bite registration cap 24. The patient then closes his mouth until the rest of the patient's teeth are in occlusion. The selective angular adjustability of the integral support member 44 allows for efficient adjustment and positioning of the bite recording medium, supported by bite recording cap 24, within the mouth of the patient.

It is to be understood that the present invention is not limited to the embodiments described above, but encompasses any and all embodiments within the scope of the following claims.

We claim:

1. An adjustable bite recording tool for dental implants, comprising:
   a hollow support post having opposing upper and lower ends and an annular groove defined therein adjacent the lower end;
   a screw having a head and an externally threaded shank, the screw being inserted through the hollow support post so that the threaded shank extends from the lower end of the hollow support post, the head being retained inside the hollow support post, the screw being adapted for releasably fastening the hollow support post to a patient's dental implant;
   an angularly adjustable ring rotatably seated within the annular groove;
   a support table;
   a support arm extending between the angularly adjustable ring and the support table, the support arm extending upward from the angularly adjustable ring and outward from the hollow support post at an oblique angle, the support table being substantially horizontally disposed; and
   a bite recording cap releasably mounted on the support table and on the upper end of the hollow support post, the bite recording cap having a top surface adapted for supporting a bite recording medium for forming a bite impression of a tooth positioned opposite the patient's dental implant.

2. The adjustable bite recording tool as recited in claim 1, wherein the upper end and the lower end of the hollow support post each define an opening, the opening in the upper end having a diameter dimensioned and configured for passing both the head and the shank of the screw into the hollow support post, the opening in the lower end having a diameter dimensioned and configured for extending only the shank of the screw from the lower end of the hollow support post while retaining the head within the hollow support post.

3. The adjustable bite recording tool as recited in claim 1, wherein the angularly adjustable ring, the support arm, and the support table are integrally formed with one another.

4. The adjustable bite recording tool as recited in claim 1, wherein the top surface of the bite recording cap is textured for releasably engaging the bite recording medium.

5. The adjustable bite recording tool as recited in claim 4, wherein the top surface of the bite recording cap has a plurality of recesses foilned therein.

6. The adjustable bite recording tool as recited in claim 1, wherein the bite recording cap has an upper platform portion and a cylindrical sleeve depending from the upper platform portion, the cylindrical sleeve having a recess formed therein for receiving the upper end of the hollow support post.

7. The adjustable bite recording tool according to claim 6, wherein the upper end of the hollow support post has a polygonal head, the recess in the hollow support sleeve having a polygonal shape closely conforming to the head of the hollow support post.

8. The adjustable bite recording tool according to claim 6, wherein the upper end of the hollow support post has a hexagonal head, the recess in the cylindrical sleeve having a hexagonal shape closely conforming to the head of the hollow support post.

9. The adjustable bite recording tool according to claim 1, wherein the lower end of the hollow support post has a generally frustoconical taper.

10. The adjustable bite recording tool according to claim 1, wherein the hollow support post is made of an autoclavable metal.

11. The adjustable bite recording tool according to claim 1, wherein the bite recording cap is made of plastic.

12. An adjustable bite recording tool for dental implants, comprising:
   a hollow support post having opposing upper and lower ends and an annular groove defined therein adjacent the lower end, the hollow support post having a substantially cylindrical body and a hexagonal head at the upper end;
   a screw having a head and an externally threaded shank, the screw being inserted through the hollow support post so that the threaded shank extends from the lower end of the hollow support post, the head being retained inside the hollow support post, the screw being adapted for releasably fastening the post to a patient's dental implant;
   an angularly adjustable ring rotatably seated within the annular groove;
   a support table;
   a support arm extending between the angularly adjustable ring and the support table, the support arm extending upward from the angularly adjustable ring and outward from the post at an oblique angle, the support table being substantially horizontally disposed; and
   a bite recording cap releasably mounted on the support table and on the upper end of the hollow support post, the bite recording cap having an upper platform portion and a cylindrical sleeve depending from the upper platform portion, the cylindrical sleeve having a hexagonal recess formed therein closely conforming to the head of the hollow support post, the upper platform portion having a top surface adapted for receiving a bite recording medium for forming a bite impression of a tooth positioned opposite the patient's dental implant.

13. The adjustable bite recording tool as recited in claim 12, wherein the angularly adjustable ring, the support arm, and the support table are integrally formed with one another.

14. The adjustable bite recording tool as recited in claim 12, wherein the top surface of the bite recording cap is textured for releasably engaging the bite recording medium.

15. The adjustable bite recording tool as recited in claim 12, wherein the top surface of the bite recording cap has a plurality of recesses formed therein.

16. An adjustable bite recording tool for dental implants, comprising:
   a hollow support post having opposing upper and lower ends and an annular groove defined therein adjacent the lower end;
   a screw having a head and an externally threaded shank, the screw being inserted through the hollow support post so that the threaded shank extends from the lower end of the hollow support post, the head being retained inside the hollow support post, the screw being adapted for releasably fastening the hollow support post to a patient's dental implant;
   an angularly adjustable ring rotatably seated within the annular groove;
   a support table;
   a support arm extending between the angularly adjustable ring and the support table, the support arm extending upward from the angularly adjustable ring and outward from the hollow support post at an oblique angle, the support table being substantially horizontally disposed; and
   a bite recording cap releasably mounted on the support table and on the upper end of the support post, the cap having a top surface adapted for supporting a bite recording medium for forming a bite impression of a tooth positioned opposite the patient's dental implant the top surface having a plurality of openings defined therein adapted for anchoring the bite recording medium to the top surface of the cap.

17. The adjustable bite recording tool as recited in claim 16, wherein the top surface of the bite recording cap is textured for releasably engaging the bite recording medium.

18. The adjustable bite recording tool as recited in claim 16, the hollow support post is made of an autoclavable metal and the bite recording cap is made of plastic.

19. The adjustable bite recording tool for dental implants as recited in claim 16, wherein the angularly adjustable ring, the support arm, and the support table are integrally formed with one another.

20. The adjustable bite recording tool for dental implants as recited in claim 16, wherein the bite recording cap has an upper platform portion and a cylindrical sleeve depending from the upper platform portion, the cylindrical sleeve having a recess formed therein for receiving the upper end of the hollow support post.

* * * * *